United States Patent [19]

Ikegami et al.

[11] Patent Number: 4,533,562
[45] Date of Patent: Aug. 6, 1985

[54] METHOD OF PREPARING COATED SOLID PREPARATIONS

[75] Inventors: Yoshihiko Ikegami; Kozo Kurihara; Izuo Ichikawa; Hisanori Nakane, all of Tokyo, Japan

[73] Assignee: Sankyo Company, Limited, Tokyo, Japan

[21] Appl. No.: 601,736

[22] Filed: Apr. 19, 1984

Related U.S. Application Data

[63] Continuation of Ser. No. 366,063, Apr. 6, 1982, abandoned.

[30] Foreign Application Priority Data

Apr. 13, 1981 [JP] Japan ................................ 56-55232

[51] Int. Cl.$^3$ ........................... A61R 9/32; C08L 1/32
[52] U.S. Cl. ..................................... 427/3; 424/33; 427/195; 427/212; 427/222; 427/221; 427/202
[58] Field of Search ....................... 427/3, 4, 212, 213, 427/221, 222, 202, 195; 424/33

[56] References Cited

U.S. PATENT DOCUMENTS 2,772,181  11/1956  Rogers ................................ 427/195
4,344,979  8/1982  Gago ...................................... 427/4

FOREIGN PATENT DOCUMENTS 2122395  11/1971  Fed. Rep. of Germany .......... 427/3
WO80/00659  4/1980  PCT Int'l Appl. .

OTHER PUBLICATIONS

Myers "Film Forming Compositions" 1968, pp. 349, 356.

*Primary Examiner*—Sam Silverberg
*Attorney, Agent, or Firm*—Frishauf, Holtz, Goodman & Woodward

[57] ABSTRACT

Solid materials, especially pharmaceutical preparations, are coated, without the use of solvents, with a powdered film-forming polymer and with a liquid plasticizer having an affinity for the polymer.

22 Claims, No Drawings

METHOD OF PREPARING COATED SOLID PREPARATIONS

This is a continuation of application Ser. No. 366,063, filed Apr. 6, 1982, now abandoned.

The present invention relates to a method of preparing coated solid preparations, which avoids the need to use water or another solvent in the coating process, and is of particular value in the production of coated pharmaceutical preparations, for example pills, tablets, capsules or granules.

In recent years, many areas of industry have attempted to replace the organic solvents often used in products or in manufacturing processes by water; this tendency is particularly noted in the paint and pharmaceutical industries. In general, organic solvents are expensive (at least, when compared with water), can be unpleasant or perhaps even dangerous to work with and can give rise to problems of pollution. In the pharmaceutical industry, where tremendous quantities of solvents are used for the coating of such pharmaceutical preparations as granules, fine powders, pills, capsules or tablets, the effects of residual organic solvents in the coating of the pharmaceutical preparation on the human body constitute a further reason why a change from organic solvents to water is generally desired.

However, the most common method of coating a preparation which is soluble in the intestines or the stomach with a water-insoluble polymer is still to dissolve the polymer in an organic solvent, together with, if required, a plasticizer, a colouring agent and other conventional materials, coat the preparation with the solution and then evaporate off the solvent. This method, however, requires large quantities of organic solvents and thus gives rise to the aforementioned disadvantages of economy, safety and environmental pollution.

Amongst the many experiments which have been conducted to use water in place of organic solvents in such coating processes, that described in "Drug made in Germany", 16, 126 (1973) comprises the use of a coating liquid in the form of an aqueous dispersion of a methyl methacrylate/methacrylic acid copolymer formed by emulsion polymerization. This method is, however, too unsafe to use freely with pharmaceuticals, because residual emulsifying agent, polymerization initiator, monomer and oligomer in the coating can be dangerous. Moreover, the properties of the dispersion make it impossible to separate out, and perhaps purify, the polymer and then re-disperse it prior to use for coating pharmaceutical preparations. Finally, a further disadvantage is that this aqueous dispersion is unstable to various physical changes, such as temperature change, mixing or dispersing, any of which can give rise to irreversible coagulation and separation.

Another coating method using water has been proposed by Shinetsu Chemical Industry Co. Ltd. An enteric preparation is obtained by coating the pharmaceutical first with an aqueous solution of the water-soluble polymer hydroxypropyl methylcellulose and then with a coating liquid which comprises hydroxypropyl methylcellulose phthalate (an enteric polymer) dispersed in water and a plasticizer. This process uses powdered hydroxypropyl methylcellulose phthalate and plasticizer dispersed or partly dissolved in water and, as with the previously discussed proposal, the dispersion is unstable to physical changes, such as a temperature rise; if the temperature rises above 20° C., coagulation and sedimentation occur.

As is apparent from the above discussion, a disadvantage of coating methods using water as the dispersion medium arises from the fact that dispersions of a water-insoluble polymer in water tend to be unstable. Moreover, the use of water as a solvent or dispersion medium requires the consumption of a large amount of energy in a drying process and there may be the risk of damaging the active ingredient of the preparation, when the said ingredient is unstable to moisture.

Accordingly, some proposals have been made for coating methods which completely avoid the use of solvents. In one such method, a thermoplastic or thermo-melting material, such as wax, is applied by spraying or by melting and causing it to adhere to a previously heated material which it is desired to coat. This method has the disadvantage that the coating material is limited to materials which can melt or are thermoplastic, such as wax, and there are few materials which can be used within the temperature range of from 20° C. to 70° C., which is commonly employed in the coating of pharmaceuticals.

Another solventless coating method comprises charging a powdered coating material and the material to be coated with static electricity, to cause the coating material to adhere. This has the disadvantage that charging these materials with static electricity requires the use of very expensive equipment.

In summary, of the three types of technique which have been proposed, the old-established technique of using organic solvents is inherently undesirable and can be expensive, the technique using water is difficult to operate and can give rise to stability problems (especially when used with pharmaceuticals) and the solventless techniques are limited in their application or are prohibitively expensive.

There is, therefore, a need to provide a relatively inexpensive coating technique which avoids the safety problems of the technique using organic solvents, avoids the various stability problems of the technique using water and avoids the problems associated with the known solventless techniques.

Accordingly, the present invention provides a method of coating a solid material, in which said material is coated with a powdered film-forming polymer and with a liquid plasticizer having an affinity for said polymer.

In carrying out the method of the invention, we prefer that the plasticizer should first be coated over the surface of the solid material and that the powdered polymer should be applied afterwards. If necessary, the coated preparation can be heated to cause the polymer to form a film over the surface of the solid preparation.

Since the coating produced by a single application of the method of the invention may be relatively thin, we prefer to repeat the coating steps a number of times in order to build up a number of coats on the solid material. In general, we prefer to apply from 5 to 20 separate coats, conveniently about 10 coats.

The plasticizer, being applied in liquid form, is preferably sprayed onto the solid material to be coated, whilst the polymer, being in powdered form, is preferably dusted on. Any conventional coating apparatus may be used to provide an essentially even coating, for example a centrifugal granulator, a coating pan or a fluidised bed granulator, although the coating pan and the centrifugal granulator are preferred.

Any kind of polymer which can be supplied in powdered form and which is capable of forming a film may be used as the material for the coating in the method of the present invention. The nature of the polymer employed will, of course, depend upon the ultimate use to which the coated material produced by the method of the invention is to be put. For example, in the case of a pharmaceutical preparation, it may be desirable to provide, as the coating, an enteric polymer or a polymer soluble in the stomach. For certain pharmaceutical applications and for other purposes, it may be desirable to use a water-soluble polymer, a polymer soluble in both water and organic solvents or a polymer soluble in organic solvents but not in water. Mixtures of these various different types of polymers may also be used.

Examples of enteric polymers include hydroxypropyl methylcellulose phthalate, cellulose acetate phthalate, methyl methacrylate/methacrylic acid copolymer, polyvinyl acetate phthalate, carboxymethyl ethylcellulose, polyvinyl alcohol phthalate, starch acetate phthalate, cellulose acetate succinate and styrene/maleic acid copolymer.

Examples of polymers soluble in the stomach include polyvinyl acetal diethylaminoacetate, poly(dimethylaminoethyl methacrylate), benzylaminomethylcellulose, diethylaminomethylcellulose, benzylaminoethyl hydroxyethylcellulose, cellulose acetate diethylaminoacetate and cellulose acetate dibutylaminohydroxypropyl ether.

Examples of water-soluble polymers include sodium carboxymethylcellulose, methylcellulose, hydroxyethylcellulose, polyvinyl alcohol and gelatin.

Examples of polymers soluble in both water and organic solvents include polyvinylpyrrolidone, pyrrolidone/vinyl acetate copolymer, polyethylene glycol, hydroxypropyl methylcellulose, hydroxypropylcellulose and vinylpyrrolidone/vinyl acetate copolymer.

Examples of polymers soluble in organic solvents but not in water include ethylcellulose, methylvinylpyridine/methyl acrylate methacrylate copolymer, acetylcellulose, nitrocellulose, polyvinyl acetate and shellac.

A single one of these polymers or a mixture of two or more may be used. Where a mixture of polymers is used, the polymers of the mixture may all have the same type of solubility, e.g. they may all be water-soluble polymers, or, for special purposes, mixtures of polymers having different types of solubility may be employed. The polymers must be used in the form of a powder as this enables a far better film to be formed. In general, we prefer that the particles of the powder should have a particle diameter less than 100 μm, more preferably less than 30 μm. Powders of smaller particle diameter will generally give a better coating and, accordingly, for some purposes, it may be desirable to use a powder of even smaller particle diameter, e.g. less than 10 μm.

The powdered polymer may be prepared by any known technique, e.g. pulverization or various chemical procedures, such as that disclosed in Japanese patent application Kokai (i.e. as laid open to public inspection) No. 55-54331 and the way in which the polymer is brought to its powdered state is not critical to the present invention.

The plasticizer used in the method of the invention must have an affinity for the polymer. By "affinity" we mean that the liquid plasticizer must be capable of swelling or dissolving the powdered polymer used for coating. The plasticizer preferably has a boiling point higher than 100° C. and must be in the liquid state at the time of use. Plasticizers which are solid at ambient temperatures can be heated and melted in order that they may be used in the liquid state; in general, it is easier to find plasticizers capable of melting at relatively low temperatures than it is to find coating polymers capable of doing the same.

Examples of plasticizers which may be used in the method of the invention include: glycerol esters, such as triacetin, glycerol monocaprylate and monoalkyl esters of diacetin; phthalic acid esters, such as dibutyl phthalate; alcohols, such as glycerol or diacetone alcohol; glycols such as propylene glycol, polyethylene glycol 400 or polyethylene glycol 4000; polyoxyethylene alkyl esters, especially polysorbates, such as polyoxyethylene sorbitan monooleate; and sorbitan fatty acid esters, such as sorbitan trioleate. These plasticizers may be applied by spraying or, if they have a high melting point, they may be applied in powdered form and then heated to cause them to liquify.

The amount of plasticizer to be used will vary depending upon the polymer or polymers chosen, but, in general, the plasticizer will be used in an amount less than one half of the weight of the polymer.

Colouring agents, perfumes, pigments, waxes and other conventional additives may be incorporated into the coating or into any ingredient of the coating, should it be desired.

The method of the invention is applicable to all types of solid material, whatever their ultimate use, but it is of particular value in coating pharmaceutical preparations. The solid material may, for example, be in the form of granules, fine powders, pills, capsules or tablets. If desired, it is possible to carry out a conventional coating process prior to the method of the invention, so that a coating applied by the method of the invention is provided on top of a conventionally applied coating.

Upon completion of the coating operation, the coated material may, if desired, be subjected to various conventional treatments, including polishing, sugar-coating or coating with other materials.

The invention further illustrated by the following nonlimiting Examples.

In the Examples, all parts and percentages are by weight and the mesh sizes are all Tyler standard.

EXAMPLE 1

(a) Preparation of Tablets

50 Parts of lactose, 20 parts of micro crystalline cellulose, 20 parts of calcium carboxymethylcellulose and 10 parts of S-benzoylthiamine monophosphate were mixed for about 3 minutes in a Henschel mixer, after which a 7% aqueous solution of hydroxypropylcellulose was added, and the mixture was kneaded. The kneaded mixture was then pulverized in a Tornado mill (manufactured by F. J. Stokes Co. Ltd) provided with a screen having 10 mm square apertures, after which it was dried in a air dryer at 60° C. for 2 hours. The dried substance was then further pulverized in a Toronado mill provided with a screen having 2 mm diameter apertures. The granules thus obtained were mixed with magnesium stearate in a amount equivalent to 0.5% and tablets were produced from the resulting mixture using a punch having a punch diameter of 8 mm and a radius of curvature of 10 mm. Each tablet weighed 200 mg. These tablets would disintegrate in about 3 minutes in water, using the disintegration test apparatus prescribed by The Pharmacopoeia of Japan, ninth Edition (1976), English Edition published by the Society of Japanese Pharmacopoeia Yakuji Nippo, Ltd. (hereinafter "the Japanese Pharmacopoeia ninth Edition").

(b) Coating 500 g of the tablets obtained in step (a) were introduced into a centrifugal granulator, where they were coated with a solution of 10 g of polyethylene glycol 6000 in 10 g of water. The tablets were then heated to about 4° C. by blowing hot air.

After discontinuing the hot air, about 1.5 g of triacetin was sprayed onto the tablets, and then about 5 g of hydroxypropyl methylcellulose phthalate HP-55F (manufactured by Shinetsu Chemical Industry Co. Ltd, this is a powder having a particle diameter of about 12 μm) were dusted onto the tablets. After rotation for about 3 minutes, the product was again heated to about 40° C. by blowing hot air. After discontinuing the hot air, the sequence of spraying with 1.5 g of triacetin, dusting with 5 g of hydroxypropyl methylcellulose phthalate, rotation and blowing hot air was repeated to a total of 10 times, thus coating the 500 g of tablets with 10 g of polyethylene glycol 6000, 15 g of triacetin and 50 g of hydroxypropyl methylcellulose phthalate. In a final step, about 3 g of talc were dusted onto the tablets, to prevent them from adhering to each other.

(c) Test

The tablets prepared in step (b) were subjected to a disintegration test for enteric tablets according to the method of the Japanese Pharmacopoeia ninth Edition using either the first liquid prescribed by said Pharmacopoeia or a mixture of the first and second liquids which was adjusted to a pH value of 4.0. No disintegration was observed after 120 minutes. In the course of this test, the test solution was circulated through a flow cell, which was examined by means of a photospectrometer, to determine whether there was any elution of the S-benzoylthiamine monophosphate. No elution was observed.

Using the second liquid of said Pharmacopoeia alone, the tablets disintegrated within 6 minutes.

The first liquid of said Pharmacopoeia is prepared by dissolving 2.0 g of sodium chloride in 24.0 ml of dilute hydrochloric acid and adding sufficient water to make 1000 ml. This solution is transparent and colourless and its pH value is about 1.2.

The second liquid is prepared by dissolving 35.8 g of disodium hydrogen phosphate in 6.0 ml of dilute hydrochloric acid and adding sufficient water to make 1000 ml. This solution is transparent and colourless and its pH value is about 7.5.

EXAMPLE 2

(a) Coating 500 g of tablets prepared as described in Example 1 (a) were introduced into a coating pan and heated tq about 40° C. by blowing them with hot air. After stopping the hot air, 1.5 g of propylene glycol was sprayed onto the tablets, and then about 5 g of hydroxypropyl methylcellulose phthalate HP-55F were dusted on. After rotating the pan for about 3 minutes, the product was heated to about 40° C. by blowing it with hot air. After discontinuing the hot air, this sequence of spraying with 1.5 g of propylene glycol, dusting with 5 g of hydroxypropyl methylcellulose phthalate, rotation and blowing with hot air was repeated once.

1.5 g of glycerol monocaprylate (manufactured by Nikko Chemical K.K.) was sprayed onto the tablets, and then about 5 g of hydroxypropyl methylcellulose phthalate HP-55F were dusted on. After rotating the pan for about 3 minutes, the product was again heated to about 40° C. by blowing it with hot air. After discontinuing the hot air, this sequence of spraying with 1.5 g of glycerol monocaprylate, dusting with 5 g of hydroxypropyl methylcellulose phthalate, rotation and blowing with hot air was repeated to a total of 10 times, thus coating the 500 g of tablets with 3 g of propylene glycol, 15 g of glycerol monocaprylate and 50 g of hydroxypropyl methylcellulose phthalate.

The coating was then completed by dusting the tablets with about 3 g of talc, to prevent them from adhering to each other.

(b) Test

The tablets obtained in step (a) were then subjected to a disintegration test for enteric tablets according to the method of the Japanese Pharmacopeia ninth Edition, using a mixture of the first and second solutions which had been adjusted to a pH value of 4.0. No disintegration was observed after 120 minutes.

In the second solution of the Pharmacopeia, the tablets disintegrated within 6 minutes.

EXAMPLE 3

(a) Coating 500 g of tablets produced as described in Example 1 (a) were introduced into a coating pan and heated to about 40° C. by blowing them with hot air. After discontinuing the hot air, about 1.5 g of propylene glycol was sprayed onto the tablets, and then about 5 g of hydroxypropyl methylcellulose phthalate HP-55F were dusted on. After rotating the pan for about 3 minutes, the product was again heated to about 40° C. by blowing it with hot air. After discontinuing the hot air, the sequence of spraying with 1.5 g of propylene glcyol, dusting with 5 g of hydroxypropyl methylcellulose phthalate, rotation and blowing with hot air was repeated to a total of about 10 times, to coat the 500 g of tablets with 15 g of propylene glycol and 50 g of hydroxypropyl methylcellulose phthalate.

(b) Test

The surface and a cross-section of the tablets produced in step (a) were observed under an optical microscope and under a scanning electron microscope, both of which confirmed that the tablets had a uniform film coating.

EXAMPLE 4

(a) Coating 500 g of tablets prepared as described in Example 1 (a) were introduced into a coating pan and heated to about 60° C. by blowing them with hot air. About 1.5 g of polyethylene glycol 4000, which had previously been melted at about 60° C., was then sprayed onto the tablets. After rotating the pan for about 2 minutes, the tablets were then dusted with about 5 g of hydroxypropyl methylcellulose phthalate HP-55F and the pan was again rotated for about 3 minutes. This sequence of spraying with 1.5 g of polyethylene glycol 4000, rotation, dusting with 5 g of hydroxypropyl methylcellulose phthalate and rotation was repeated to a total of 10 times, to coat the 500 g of tablets with 15 g of polyethylene glycol 4000 and 50 g of hydroxypropyl methylcellulose phthalate.

The coating was completed by dusting the tablets with about 3 g of talc, to prevent them from adhering to each other.

(b) Test

The surfaces and a cross-section of the coated tablets were observed with an optical microscope and with a scanning electron microscope, confirming that the tablets had a uniform film coating.

EXAMPLE 5

(a) Pulverization of polyethylene glycol

Polyethylene glcyol 4000 was pulverized in a fluid energy mill, type PJM-100 NP (manufactured by Nippon Pneumatic Industry K.K.) at an air pressure of 6.0 kg/cm$^2$ gauge, to give a powder of particle diameter about 10 μm.

(b) Coating 500 g of tablets prepared as described in Example 1 (a) were introduced into a coating pan, followed by 2.5 g of pulverized polyethylene glycol 4000, obtained as described in step (a). Whilst the pan was being rotated, hot air was blown from outside the pan onto its contents to heat them to about 60° C. and thus to liquefy the polyethylene glycol 4000; the surfaces of the tablets were wetted with the resulting liquid. 5 g of hydroxypropyl methylcellulose phthalate HP-55F were then dusted onto the tablets and, after rotating the pan for about 3 minutes, the sequence of adding 2.5 g of pulverized polyethylene glycol 4000, heating to about 60° C. with rotation, dusting with about 5 g of hydroxypropyl methylcellulose phthalate and rotation was repeated to a total of about 10 times, to coat the 500 g of tablets with 25 g of polyethylene glycol 4000 and 50 g of hydroxypropyl methylcellulose phthalate.

The coating was then completed by dusting the tablets with about 3 g of talc to prevent them from adhering to each other.

(c) Test

The surface and a cross-section of the coated tablets were observed through an optical microscope and through a scanning electron microscope, which observations confirmed that the tablets had a uniform film coating.

EXAMPLE 6

(a) Coating 500 g of tablets prepared as described in Example 1 (a) were introduced into a coating pan and heated to about 40° C. by blowing them with hot air. After discontinuing the hot air, the tablets were sprayed with about 1.5 g of polyoxyethylene sorbitan monooleate (manufactured under the trade mark Tween 80 by Kao Atlas K.K.) and they were then dusted with about 5 g of hydroxypropyl methylcellulose phthalate HP-55F. After rotating the pan for about 3 minutes, the product was again heated to about 40° C. by blowing it with hot air. After discontinuing the hot air, this sequence of spraying with 1.5 g of polyoxyethylene sorbitan monooleate, dusting with about 5 g of hydroxypropyl methylcellulose phthalate, rotation and blowing with hot air was repeated to a total of about 10 times, to coat the 500 g of tablets with 15 g of polyoxyethylene sorbitan monooleate and 50 g of hydroxypropyl methylcellulose phthalate.

The coating was completed by dusting the tablets with about 3 g of talc, to prevent them from adhering to each other.

(b) Test

The surface and a cross-section of the coated tablets obtained in step (a) were observed through an optical microscope and through a scanning electron microscope, these observations confirming that the tablets had a uniform film coating.

EXAMPLE 7

(a) Preparation of a fine enteric polymer powder

This preparation was carried out essentially in accordance with the method described in Japanese patent application Kokai No.55-54331.

Water was added to 1249 ml of a 0.5N aqueous solution of sodium hydroxide, to give 7750 ml of a solution. 20 g of sodium lauryl sulphate were then added to this solution and dissolved in it. 250 g of hydroxypropyl methylcellulose phthalate HP-55 were dissolved in the solution and insolubles were removed using a 100 mesh sieve. Whilst maintaining the solution at a temperature below 30° C. and agitating it with a TK Homo-mixer (manufactured by Tokushu Kika Kogyo K.K.), it was neutralized by gradually adding 1249 ml of 0.5N hydrochloric acid, giving a hydrosol of hydroxypropyl methylcellulose phthalate. This hydrosol was heated over a water bath whilst being agitated by a TK Homo-mixer, and solid particles began to precipitate at about 65° C. The solution was further heated to 75° C., agitated for 5 minutes and then cooled to about room temperature.

The resulting solid particles were dispersed and diluted in purified water (in an amount of about 20 times the volume of the particles) to give a dispersion, from which the solid particles were separated and collected by centrifugation. This washing operation was repeated two more times, and then the solid particles were dried with an air drier at 60° C. for 2 hours.

The particle diameter of the hydroxypropyl methylcellulose phthalate powder thus obtained was about 4 μm.

(b) Coating 500 g of tablets prepared as described in Example 1 (a) were introduced into a coating pan and heated to about 40° C. by blowing them with hot air. After discontinuing the hot air, the tablets were sprayed with 3 g of propylene glycol and then dusted with about 10 g of the hydroxypropyl methylcellulose phthalate powder obtained in step (a). The pan was rotated for about 3 minutes and then the product was heated again to about 40° C. by blowing with hot air.

After discontinuiqg the hot air, the tablets were sprayed with about 1.5 g of triacetin and then dusted with about 5 g of the hydroxypropyl methylcellulose phthalate powder prepared in step (a). The pan was rotated for another 3 minutes and the product was again heated to about 40° C. by blowing it with hot air.

After discontinuing the hot air, the sequence of spraying with 1.5 g of triacetin, dusting with about 5 g of hydroxypropyl methylcellulose phthalate, rotation and heating was repeated to a total of about 10 times, to coat the 500 g of tablets with 3 g of propylene glycol, 15 g of triacetin and 50 g of hydroxypropyl methylcellulose phthalate.

The coating was completed by dusting the tablets with about 3 g of talc, to prevent them from adhering to each other.

(c) Test

The coated tablets obtained in step (b) were subjected to disintegration tests for enteric tablets, as prescribed in the Japanese Pharmacopeia ninth Edition, using either the first liquid or a mixture of the first and second liquids adjusted to a pH value of 4.0. Even after 120 minutes, no disintegration was observed. In the course of the test, the test solutions were circulated through a flow cell and examined by a photospectrometer, to determine whether any S-benzoylthiamine monophosphate was eluted; no elution was observed. In the second solution of the Pharmacopeia and in a mixture of the first and second solutions adjusted to a pH value of 6.0, disintegration occurred within 5 minutes and 7 minutes, respectively.

EXAMPLE 8

(a) Preparation of a fine enteric polymer powder

This preparation employed the method disclosed in Japanese patent application Kokai No. 55-54331.

Sufficient water was added to 2580 ml of a 0.5N aqueous solution of sodium hydroxide to give about 50 liters of solution, to which was then added 1.0 g of silicone oil KS-66 antifoaming agent (manufactured by Shinetsu Chemical Industry Co. Ltd). 100 g of the surface active agent, sodium lauryl sulphate, were then dissolved in the solution, followed by 500 g of carboxymethyl ethylcellulose (CMEC, pH 5.0, manufactured by Freund Sangyo K.K.). The insolubles were removed using a 100 mesh sieve. The solution was maintained at a temoerature below 30° C. and neutralized by gradually adding, with stirring, 2580 ml of 0.5N hydrochloric acid. The resulting hydrosol of carboxymethyl ethylcellulose was agitated in a TK Agi-Homo-mixer, heated at 75° C. for 5 minutes, and then cooled to room temperature. The solid particles were separated and collected by centrifugation and then washed by repeating 3 times the steps of diluting and dispersing them in purified water and centrifugation. After this, the particles were dried in an air drier at 60° C. for 1 hour to obtain a fine powder of carboxymethyl ethylcellulose having a particle diameter of about 3 μm.

(b) Coating 500 g of tablets prepared as described in Example 1 (a) were introduced into a coating pan and heated to about 40° C. by blowing them with hot air. After discontinuing the hot air, the tablets were sprayed with 3.0 g of propylene glycol and then dusted with about 10 g of the fine carboxymethyl ethylcellulose powder prepared in step (a). The pan was then rotated for about 3 minutes and the product was again heated to about 40° C. by blowing hot air onto it.

After discontinuing the hot air, the product was sprayed with about 1.5 g of triacetin, and then about 5 g of the fine carboxymethyl ethylcellulose powder prepared in step (a) was dusted onto it. The pan was rotated for another 3 minutes and then the product was heated to about 40° C. by blowing it with hot air. This sequence of spraying with 1.5 g of triacetin, dusting with about 5 g of carboxymethyl ethylcellulose, rotation and blowing with hot air was repeated to a total of about 10 times, to coat the 500 g of tablets with 3 g of propylene glycol, 15 g of triacetin and 50 g of carboxymethyl ethylcellulose.

The coating was completed by dusting the tablets with about 3 g of talc, to prevent the tablets from adhering to each other.

(c) Test

The coated tablets obtained in step (b) were subjected to disintegration tests, as prescribed for enteric tablets in the Japanese Pharmacopeia ninth Edition, using either the first solution or a mixture of the first and second solutions adjusted to a pH value of 4.0. Even after 120 minutes, no disintegration was observed. On the other hand, in the second solution of the Pharmacopeia, disintegration occurred within 5 minutes.

EXAMPLE 9

(a) Pulverization of a stomach-soluble polymer

Polyvinyl acetal diethylaminoacetate AEA "Sankyo" was pulverized using a fluid energy mill, type PJM-100 NP, under an air pressure of 6.0 kg/cm² gauge, to give a powder of particle diameter about 20 μm.

(b) Coating 500 g of tablets prepared as described in Example 1 (a) were introduced into a coating pan and heated to about 40° C. by blowing them with hot air. After discontinuing the hot air, the tablets were sprayed with about 1.5 g of triacetin and then dusted with about 5 g of the pulverized polyvinyl acetal diethylaminoacetate prepared in step (a). The pan was rotated for about 3 minutes, and then the product was again heated to about 40° C. by blowing it with hot air. After discontinuing the hot air, the sequence of spraying with about 1.5 g of triacetin, dusting with about 5 g of polyvinyl acetal diethylaminoacetate, rotation and blowing with hot air was repeated to a total of about 10 times, to coat the 500 g of tablets with 15 g of triacetin and 50 g of polyvinyl acetal diethylaminoacetate.

The coating was completed by dusting the tablets with about 3 g of talc, to prevent them from adhering together.

(c) Test

The coated tablets obtained in step (b) were subjected to a disintegration test using water and the apparatus prescribed in the Japanese Pharmacopeia ninth Edition. Even after 60 minutes, no disintegration could be observed. On the other hand, using the first solution of the Pharmacopeia, disintegration occurred within 5 minutes.

EXAMPLE 10

(a) Preparation of plasticizer 80 parts of triacetin and 20 parts of a mixture of monoalkyl esters of diacetin (available under the trade name "Myvacet" from Eastman Kodak Co., U.S.A.) were charged into a beaker and stirred with a magnetic stirrer to prepare a uniform mixture of plasticizers.

(b) Coating 500 g of tablets prepared as described in Example 1 were introduced into a coating pan and heated to about 40° C. by blowing them with hot air. After discontinuing the hot air, the tablets were sprayed with about 1.5 g of the plasticizer mixture prepared as described in step (a) and then dusted with about 5 g of pulverized polyvinyl acetal diethylaminoacetate, prepared as described in Example 9 (a). The pan was rotated for about 3 minutes and then the product was again heated to about 40° C. by blowing it with hot air.

After discontinuing the hot air, the sequence of spraying with about 1.5 g of plasticizer mixture, dusting with about 5 g of pulverized polyvinyl acetal diethylaminoacetate, rotation and blowing with hot air was repeated to a total of about 10 times, to coat the 500 g of tablets with 15 g of plasticizer mixture and 50 g of polyvinyl acetal diethylaminoacetate.

The coating was completed by dusting the tablets with about 3 g of talc, to prevent them from adhering to each other.

(c) Test

The coated tablets obtained in step (b) were subjected to a disintegration test using water and the apparatus prescribed by the Japanese Pharmacopeia ninth Edition. Even after 60 minutes, no disintegration could be observed. On the other hand, a similar test using the first solution of the Pharmacopeia showed disintegration within 5 minutes.

EXAMPLE 11

(a) Preparation of polymer powder 50 parts of pulverized polyvinyl acetal diethylaminoacetate, prepared as described in Example 9 (a), and 50 parts of pulverized ethylcellulose, prepared as described in Example 14 (a), were mixed in a twin shell mixer, to prepare a mixed polymer powder.

(b) Coating 500 g of tablets prepared as described in Example 1 were introduced into a coating pan and heated to about 40° C. by blowing hot air onto them. After discontinuing the hot air, the tablets were sprayed with about 1.5 g of triacetin and then dusted with about 5 g of the polymer powder prepared in step (a). The pan was rotated for about 3 minutes, and then the product was heated to about 40° C. by blowing hot air onto it. After discontinuing the hot air, the sequence of spraying with about 1.5 g of triacetin, dusting with about 5 g of the polymer powder, rotation and heating were repeated to a total of about 10 times, to coat 500 g of the tablets with 15 g of triacetin and 50 g of the polymer mixture.

(c) Test

The surface and a cross-section of the tablets obtained in step (b) were observed by means of an optical microscope and a scanning electron microscope. These observations confirmed that the tablets had a uniform film coating.

EXAMPLE 12

(a) Preparation of coating powder

Fumaric acid (manufactured by Japan Catalytic Chemical Industry Co., Ltd.) was pulverized using an Atomizer KII-1 (manufactured by Fuji Denki Kogyo K.K.), to a particle diameter of about 10 μm. 8.3 parts of the resulting pulverized fumaric acid and 91.7 parts of pulverized polyvinyl acetal diethylaminoacetate, prepared as described in Example 9 (a), were then mixed, using a Henschel mixer, type FM 20/B (manufactured by Mitsui Miike Machinery Co., Ltd.) to give coating powder. The presence of fumaric acid in this powder renders water-soluble the coating film prepared from it.

(b) Coating 500 g of tablets prepared as described in Example 1 (a) were introduced into a coating pan and heated to about 40° C. by blowing them with hot air. After discontinuing the hot air, the tablets were sprayed with about 1.5 g of triacetin and then dusted with about 5 g of the coating powder prepared in step (a). The pan was rotated for about 3 minutes and then the product was heated to about 40° C. by blowing hot air onto it.

After discontinuing the hot air, the sequence of spraying with about 1.5 g of triacetin, dusting with about 5 g of coating powder, rotation and heating was repeated to a total of about 10 times, to coat 500 g of the tablets with 15 g of triacetin and 50 g of the coating powder.

The coating was completed by dusting the tablets with about 3 g of talc, to prevent them from adhering to each other.

(c) Tests

The surface and a cross-section of the coated tablets obtained in step (b) were observed through an optical microscope and through a scanning electron microscope. These observations confirmed that the tablets had a uniform film coating.

The tablets were also subjected to disintegration tests using the apparatus of the Japanese Pharmacopeia ninth Edition and either water or the first solution and disintegrated within 7 minutes and 5 minutes, respectively.

EXAMPLE 13

(a) Preparation of coating powder

A vinylpyrrolidone/vinyl acetate copolymer (manufactured by General Aniline and Film Corporation, New York, U.S.A. under the designation S-630) was passed through a 200 mesh sieve to give a powder of particle diameter about 30 μm.

(b) Coating 500 g of tablets prepared as described in Example 1 (a) were introduced into a coating pan and heated to about 40° C. by blowing them with hot air. After discontinuing the hot air, the tablets were sprayed with about 1.5 g of triacetin and then dusted with about 5 g of a vinylpyrrolidone/vinyl acetate copolymer powder, prepared as described in step (a). The pan was rotated for about 3 minutes, and then the product was heated to about 40° C. by blowing hot air onto it.

After discontinuing the hot air, the sequence of spraying with about 1.5 g of triacetin, dusting with about 5 g of copolymer powder, rotation and heating was repeated to a total of about 10 times, to coat the 500 g of tablets with 15 g of triacetin and 50 g of vinylpyrrolidone/vinyl acetate copolymer.

The coating was completed by dusting the tablets with about 3 g of talc, to prevent them from adhering to each other.

(c) Test

The surface and a cross-section of the coated tablets prepared as described in step (b) were observed through an optical microscope and through a scanning electron microscope. These observations confirmed that the tablets had a uniform film coating.

EXAMPLE 14

(a) Pulverization of ethylcellulose

Ethylcellulose 10 CPS (manufactured by The Dow Chemical Company) was pulverized using a fluid energy mill, type PJM-100 NP, under an air pressure of 6.0 kg/cm$^2$ gauge, to a particle diameter of about 20 μm.

(b) Coating 500 g of tablets prepared as described in Example 1 (a) were introduced into a coating pan and heated to about 40° C. by blowing them with hot air. After discontinuing the hot air, the tablets were sprayed with about 1.5 g of polyethylene glycol 400 and then dusted with about 5 g of pulverized ethylcellulose, prepared as described in step (a). The pan was rotated for about 3 minutes, and then the tablets were heated to about 40° C. by blowing hot air onto them.

After discontinuing the hot air, the sequence of spraying with about 1.5 g of polyethylene glycol 400, dusting with about 5 g of pulverized ethylcellulose, rotation and heating was repeated to a total of about 10 times, to coat the 500 g of tablets with 15 g of polyethylene glycol 400 and 50 g of ethylcellulose.

(c) Test

The surface and a cross-section of the coated tablets prepared as described in step (b) were observed through an optical microscope and through a scanning electron microscope. These observations confirmed that the tablets had a uniform film coating.

EXAMPLE 15

(a) Preparation of particles to be coated 40 parts of lactose, 20 parts of crystalline cellulose, 20 parts of carboxymethylcellulose and 20 parts of S-benzoylthiamine monophosphate were mixed in a Henschel mixer for about 3 minutes, after which a 7% aqueous solution of hydroxypropylcellulose was added and the whole mixture was kneaded. The kneaded mass was extruded through a granulator provided with a screen having apertures of diameter 1 mm, to form cylindrical granules. These wet granules were then formed into spherical particles using a Marumerizer granulator (manufactured by Fuji Denki Kogyo K.K.) and dried in an air dryer at 60° C. for 2 hours to give the desired particles of particle size 14/25 mesh.

(b) Coating 200 g of particles prepared as described in step (a) were charged into a centrifugal granulator, where they were coated with a solution of 12 g of polyethylene glycol 6000 in 12 g of water. Hot air was blown onto the product to heat it to about 40° C.

After discontinuing the hot air, the particles were sprayed with about 2.4 g of triacetin and then dusted with about 6 g of hydroxypropyl methylcellulose phthalate HP-55F. The pan was rotated for about 3 minutes and then the product was again heated to about 40° C. by blowing hot air.

After discontinuing the hot air, the sequence of spraying with about 2.4 g of triacetin, dusting with about 6 g of hydroxypropyl methylcellulose phthalate, rotation and heating was repeated to a total of about 10 times, to coat the 200 g of particles with 24 g of triacetin and 60 g of hydroxypropyl methylcellulose phthalate.

The coating was completed by dusting the particles with about 5 g of talc, to prevent them from adhering to each other.

(c) Test

The coated particles prepared as described in step (b) were subjected to disintegration tests for enteric granules according to the procedure prescribed by the Japanese Pharmacopeia ninth Edition, using either the first solution or a mixture of the first and second solutions adjusted to a pH value of 4.0. Even after 120 minutes, there was no observable disintegration. In the course of the test, the test solution was circulated through a flow cell, where it was examined with a photospectrometer, to determine whether there was any elution of S-benzoylthiamine monophosphate; no elution could be observed.

On the other hand, the particles disintegrated within 6 minutes and 8 minutes, respectively, in the second solution of the Pharmacopeia and in a mixture of the first and second solutions adjusted to a pH value of 6.0.

EXAMPLE 16

(a) Coating 200 g of particles prepared as described in Example 15 (a) were introduced into a coating pan with a solution containing 12 g of polyethylene glycol 6000 and 12 g of water. Hot air was blown onto the mixture, to heat the product to about 40° C.

After discontinuing the hot air, the product was sprayed with about 2.4 g of glycerol monocaprylate (manufactured by Nikko Chemicals K.K.), and then dusted with about 6 g of hydroxypropyl methylcellulose phthalate HP-55F. The pan was rotated for about 3 minutes, and then the product was heated to about 40° C. by blowing hot air onto it.

After discontinuing the hot air, the sequence of spraying with about 2.4 g of glycerol monocaprylate, dusting with about 6 g of hydroxypropyl methylcellulose phthalate, rotation and heating was repeated to a total of about 10 times, to coat the 200 g of particles with 12 g of polyethylene glycol 6000, 24 g of glycerol monocaprylate and 60 g of hydroxypropyl methylcellulose phthalate.

The coating was completed by dusting the particles with about 5 g of talc, to prevent them from adhering to each other.

(b) Test

Coated particles prepared as described in step (a) were subjected to disintegration tests for enteric granules, following the procedures prescribed by the Japanese Pharmacopeia ninth Edition, using either the first solution or a mixture of the first and second solutions adjusted to a pH value of 4.0. Even after 120 minutes, no disintegration could be observed.

On the other hand, the particles disintegrated within 6 minutes and 8 minutes, respectively, in the second solution of the Pharmacopeia and in a mixture of the first and second solutions adjusted to a pH value of 6.0.

We claim:

1. A method of coating a solid pharmaceutical preparation consisting essentially of first coating said solid pharmaceutical preparation with a liquid plasticizer and then coating with a powdered film-forming polymer, said liquid plasticizer swelling or dissolving said polymer whereby said powdered polymer particles are plasticized and form a substantially uniform coating on said solid pharmaceutical preparation.

2. A method as claimed in claim 1, wherein said polymer is selected from the group consisting of hydroxypropyl methylcellulose phthalate, cellulose acetate phthalate, methyl methacrylate/methacrylic acid copolymer, polyvinyl acetate phthalate, carboxymethyl ethylcellulose, polyvinyl alcohol phthalate, starch acetate phthalate, cellulose acetate succinate, styrene/maleic acid copolymer, polyvinyl acetal diethylaminoacetate, poly(dimethylaminoethyl methacrylate), benzylaminomethylcellulose, diethylaminomethylcellulose, benzylaminoethyl hydroxyethylcellulose, cellulose acetate diethylaminoacetate, cellulose acetate dibutylaminohydroxypropyl ether, sodium carboxymethylcellulose, methylcellulose, hydroxyethylcellulose, polyvinyl alcohol, gelatin, polyvinylpyrrolidone, pyrrolidone/vinyl acetate copolymer, polyethylene glycol, hydroxypropyl methylcellulose, hydroxypropylcellulose, vinylpyrrolidone/vinyl acetate copolymer, ethylcellulose, methylvinylpyridine/methyl acrylate methacrylate copolymer, acetylcellulose, nitrocellulose, polyvinyl acetate, shellac and mixtures of two or more thereof.

3. A method as claimed in claim 1, wherein the powdered polymer has a particle size less than 100 μm.

4. A method as claimed in claim 1, wherein the powdered polymer has a particle size less than 30 μm.

5. A method as claimed in claim 1, wherein the powdered polymer has a particle size less than 10 μm.

6. A method as claimed in claim 1, wherein the plasticizer is selected from the group consisting of triacetin, glycerol monocaprylate, monoalkyl esters of diacetin, dibuty phthalate, glycerol, diacetone alcohol, propylene glycol, polyethylene glycol 400, polyethylene glycol 4000, polyoxyethylene sorbitan monooleate and sorbitan trioleate.

7. A method as claimed in claim 1, wherein the plasticizer is solid at ambient temperature and is melted prior to or after its application to said solid material but prior to coating with said powdered polymer.

8. A method as claimed in claim 1, wherein said preparation is selected from granules, fine powders, pills, capsules and tablets.

9. A method as claimed in claim 3, wherein said polymer is selected from the group consisting of hydroxypropyl methylcellulose phthalate, cellulose acetate phthalate, methyl methacrylate/methacrylic acid copolymer, polyvinyl acetate phthalate, carboxymethyl ethylcellulose, polyvinyl alcohol phthalate, starch acetate phthalate, cellulose acetate succinate, styrene/maleic acid copolymer, polyvinyl acetal diethylaminoacetate, poly(dimethylaminoethyl methacrylate), benzylaminomethylcellulose, diethylaminomethylcellulose, benzylaminoethyl hydroxyethylcellulose, cellulose acetate diethylaminoacetate, cellulose acetate dibutylaminohydroxypropyl ether, sodium carboxymethylcellulose, methylcellulose, hydroxyethylcellulose, polyvinyl alcohol, gelatin, polyvinylpyrrolidone, pyrrolidone/vinyl acetate copolymer, polyethylene glycol, hydroxypropyl methylcellulose, hydroxypropylcellulose, vinylpyrrolidone/vinyl acetate copolymer, ethylcellulose, methylvinylpyridine/methyl acrylate methacrylate copolymer, acetylcellulose, nitrocellulose, polyvinyl acetate, shellac and mixtures of two or more thereof.

10. A method as claimed in claim 9, wherein said polymer is selected from the group consisting of hydroxypropyl methylcellulose phthalate, carboxymethyl ethylcellulose, polyvinyl acetal diethylaminoacetate, vinylpyrrolidone/vinyl acetate copolymer, ethylcellulose and mixtures of two or more thereof.

11. A method as claimed in claim 3, wherein said polymer is selected from the group consisting of hydroxypropyl methylcellulose phthalate, carboxymethyl ethylcellulose, polyvinyl acetal diethylaminoacetate, vinylpyrrolidone/vinyl acetate copolymer, ethylcellulose and mixtures of two or more thereof.

12. A method as claimed in claim 3, wherein said plasticizer is selected from the group consisting of triacetin, glycerol monocaprylate, monoalkyl esters of diacetin, dibutyl phthalate, glycerol, diacetone alcohol, propylene glycol, polyethylene glycol 400, polyethylene glycol 4000, polyoxyethylene sorbitan monooleate and sorbitan trioleate.

13. A method as claimed in claim 3, wherein said plasticizer is selected from the group consisting of triacetin, glycerol monocaprylate, propylene glycol, polyethylene glycol 4000, polyoxyethylene sorbitan monooleate, monoalkyl esters of diacetin, polyethylene glycol 400 and mixtures of two or more therof.

14. A method as claimed in claim 3, wherein said powdered polymer has a particle size less than 30 μm.

15. A method as claimed in claim 14, wherein said powdered polymer has a particle size less than 10 μm.

16. A method of coating a solid pharmaceutical preparation consisting essentially of first coating said preparation with a liquid plasticizer selected from the group consisting of triacetin, glycerol monocaprylate, propylene glycol, polyethylene glycol 4000, polyoxyethylene sorbitan monooleate, monoalkyl esters of diacetin, polyethylene glycol 400 and mixtures of two or more thereof, and then with a powdered film-forming polymer having a particle diameter less than about 30μ and selected from the group consisting of hydroxypropyl methylcellulose phthalate, carboxymethyl ethylcellulose, polyvinyl acetal diethylaminoacetate, vinylpyrrolidone/vinyl acetate copolymer, ethylcellulose and mixtures of two or more thereof whereby said powdered polymer particles are plasticized and form a substantially uniform coating on said solid material.

17. A method as claimed in claim 16, wherein said polymer has a particle size less than about 10 μm.

18. A method as claimed in claim 16, wherein said pharmaceutical preparation is selected from the group consisting of granules, fine powders, pills, capsules and tablets.

19. A method as claimed in claim 1 wherein said plasticizer is in an amount less than one-half of the weight of said powdered polymer.

20. A method as claimed in claim 9 wherein said plasticizer is in an amount less than one-half of the weight of said powdered polymer.

21. A method as claimed in claim 16 wherein said plasticizer is in an amount less than one-half of the weight of said powdered polymer.

22. A method as claimed in claim 18 wherein said plasticizer is in an amount less than one-half of the weight of said powdered polymer.

* * * * *